United States Patent
Elomari et al.

(10) Patent No.: US 8,507,396 B2
(45) Date of Patent: *Aug. 13, 2013

(54) REGENERATION OF ACIDIC CATALYSTS

(75) Inventors: Saleh Elomari, Fairfield, CA (US); Thomas V. Harris, Benicia, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 469 days.

This patent is subject to a terminal disclaimer.

(21) Appl. No.: 12/763,924

(22) Filed: Apr. 20, 2010

(65) Prior Publication Data

US 2010/0248940 A1  Sep. 30, 2010

Related U.S. Application Data

(63) Continuation of application No. 11/315,749, filed on Dec. 20, 2005, now Pat. No. 7,732,363.

(51) Int. Cl.
*B01J 20/34* (2006.01)

(52) U.S. Cl.
USPC .......... 502/20; 502/150; 502/22; 502/27; 502/53; 502/29; 502/28; 502/32; 502/155; 502/162; 502/167; 423/488; 423/484; 585/723; 585/724; 585/730; 585/809; 585/741; 585/455; 585/324; 585/415; 585/457; 585/451; 585/721; 585/323; 585/319; 585/317

(58) Field of Classification Search
None
See application file for complete search history.

(56) References Cited

U.S. PATENT DOCUMENTS

| | | | |
|---|---|---|---|
| 3,474,036 A | 10/1969 | Thorn | |
| 4,098,833 A * | 7/1978 | Wristers | 585/372 |
| 4,239,927 A | 12/1980 | Brennan et al. | |
| 5,107,061 A | 4/1992 | Ou et al. | |
| 5,304,522 A * | 4/1994 | Jalkian et al. | 502/22 |
| 5,391,527 A | 2/1995 | Kojima et al. | |
| 5,716,895 A | 2/1998 | Sugi et al. | |
| 5,731,101 A | 3/1998 | Sherif et al. | |
| 5,750,455 A | 5/1998 | Chauvin et al. | |
| 6,106,789 A | 8/2000 | Thompson et al. | |
| 2003/0009061 A1 | 1/2003 | Inoue et al. | |
| 2004/0077914 A1 * | 4/2004 | Zavilla et al. | 585/737 |
| 2004/0199006 A1 | 10/2004 | Graham et al. | |

FOREIGN PATENT DOCUMENTS

WO  WO 94/13604  6/1994

OTHER PUBLICATIONS

Adams, et al., Freidal-Crafts reactions in room temperature ionic liquids, Chem. Commun. 1999, pp. 1043-1044.
Yoo, et al., Ionic liquid-catalyzed alkylation of isobutane with 2-butene, vol. 222, pp. 511-519, Journal Catalysis 2004.
Formentin, et al., Catalysis Letters, vol. 78, pp. 1-4, Mar. 2002.
Przemyslaw Kubis, Application of ionic liquids as solvents for polymerization processes, Prog. Polym. Sci. 29 (2004) 3-12.
Miron, Molecular Structure of Conjunct Polymers, Journal of Chemical and Engineering Data, vol. 8, No. 1, pp. 150-160, Jan. 1963.
Wilkes, Dialkylimidazolium Chloroaluminate Melts: A New Class of Room-Temperature Ionic Liuids for Elecrochemistry, Spectroscopy, and Synthesis.

* cited by examiner

*Primary Examiner* — Melvin C Mayes
*Assistant Examiner* — Smita Patel
(74) *Attorney, Agent, or Firm* — Susan M. Abernathy

(57) ABSTRACT

A process for regenerating a used acidic catalyst which has been deactivated by conjunct polymers by removing the conjunct polymers so as to increase the activity of the catalyst is disclosed. Methods for removing the conjunct polymers include addition of a basic reagent and alkylation. The methods are applicable to all acidic catalysts and are described with reference to certain ionic liquid catalysts.

6 Claims, 1 Drawing Sheet

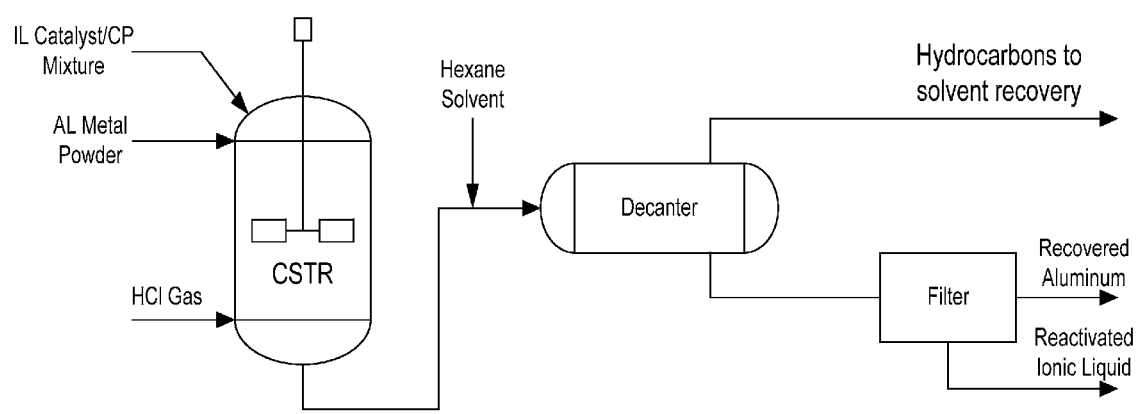

REGENERATION OF ACIDIC CATALYSTS

RELATED APPLICATION

This application is a continuation of U.S. patent application Ser. No. 11/315,749 published as US 2007-0142213 A1, herein incorporated in its entirety. The assigned art unit of U.S. patent application Ser. No. 11/315,749 is 1793.

FIELD OF THE INVENTION

The present invention relates to methods for the regeneration of catalysts and more specifically to the regeneration of acidic catalysts and to acidic ionic liquid catalysts.

BACKGROUND OF THE INVENTION

Ionic liquids are liquids that are composed entirely of ions. The so-called "low temperature" Ionic liquids are generally organic salts with melting points under 100 degrees C., often even lower than room temperature. Ionic liquids may be suitable for example for use as a catalyst and as a solvent in alkylation and polymerization reactions as well as in dimerization, oligomerization acetylation, metatheses, and copolymerization reactions.

One class of ionic liquids is fused salt compositions, which are molten at low temperature and are useful as catalysts, solvents and electrolytes. Such compositions are mixtures of components which are liquid at temperatures below the individual melting points of the components.

Ionic liquids can be defined as liquids whose make-up is entirely comprised of ions as a combination of cations and anions. The most common ionic liquids are those prepared from organic-based cations and inorganic or organic anions. The most common organic cations are ammonium cations, but phosphonium and sulphonium cations are also frequently used. Ionic liquids of pyridinium and imidazolium are perhaps the most commonly used cations. Anions include, but not limited to, $BF_4^-$, $PF_6^-$, haloaluminates such as $Al_2Cl_7^-$ and $Al_2Br_7^-$, $[(CF_3SO_2)_2N]^-$, alkyl sulphates ($RSO_3^-$), carboxylates ($RCO_2^-$) and many other. The most catalytically interesting ionic liquids are those derived from ammonium halides and Lewis acids (such as $AlCl_3$, $TiCl_4$, $SnCl_4$, $FeCl_3$ ... etc). Chloroaluminate ionic liquids are perhaps the most commonly used ionic liquid catalyst systems.

Examples of such low temperature ionic liquids or molten fused salts are the chloroaluminate salts. Alkyl imidazolium or pyridinium salts, for example, can be mixed with aluminum trichloride ($AlCl_3$) to form the fused chloroaluminate salts. The use of the fused salts of 1-alkylpyridinium chloride and aluminum trichloride as electrolytes is discussed in U.S. Pat. No. 4,122,245. Other patents which discuss the use of fused salts from aluminum trichloride and alkylimidazolium halides as electrolytes are U.S. Pat. Nos. 4,463,071 and 4,463,072.

U.S. Pat. No. 5,104,840 to describes ionic liquids which comprise at least one alkylaluminum dihalide and at least one quaternary ammonium halide and/or at least one quaternary ammonium phosphonium halide; and their uses as solvents in catalytic reactions.

U.S. Pat. No. 6,096,680 describes liquid clathrate compositions useful as reusable aluminum catalysts in Friedel-Crafts reactions. In one embodiment, the liquid clathrate composition is formed from constituents comprising (i) at least one aluminum trihalide, (ii) at least one salt selected from alkali metal halide, alkaline earth metal halide, alkali metal pseudohalide, quaternary ammonium salt, quaternary phosphonium salt, or ternary sulfonium salt, or a mixture of any two or more of the foregoing, and (iii) at least one aromatic hydrocarbon compound.

Aluminum-containing catalysts are among the most common Lewis acid catalysts employed in Friedel-Craft reactions. Friedel-Craft reactions are reactions which fall within the broader category of electrophylic substitution reactions including alkylations.

Other examples of ionic liquids and their methods of preparation may also be found in U.S. Pat. Nos. 5,731,101; 6,797,853 and in U.S. Patent Application Publications 2004/0077914 and 2004/0133056.

Hydrogenation in chloroaluminate ionic liquids in the presence of an electropositive metal and HCl was reported by K. R. Seddon et al in *Chem. Commun.*, 1999, 1043-1044.

As a result of use, ionic liquid catalysts become deactivated, i.e. lose activity, and may eventually need to be replaced. However, ionic liquid catalysts are expensive and replacement adds significantly to operating expenses by in some cases requiring shut down of an industrial process. One of the heretofore unsolved problems impeding the commercial use of chloroaluminate ionic liquid catalysts has been the inability to regenerate and recycle them. The present invention provides methods to regenerate acidic chloroaluminate ionic liquid catalysts overcoming this obstacle and paving the way for the practical, commercial use of these environmentally friendly catalysts.

SUMMARY OF THE INVENTION

Among other things the present invention provides a process for regenerating a used acidic catalyst which has been deactivated by conjunct polymers by removing the conjunct polymers so as to increase the activity of the catalyst. Methods for removing the conjunct polymers include, but are not limited to, hydrogenation, addition of a basic reagent and alkylation. The methods are applicable to all acidic catalysts and are described with reference to certain ionic liquid catalysts.

BRIEF DESCRIPTION OF THE DRAWING

The FIGURE is a process diagram of an embodiment of a process in accordance with the invention.

DETAILED DESCRIPTION

The present invention relates to a process for the regeneration of spent or deactivated acidic catalysts, including acidic ionic liquid-based catalysts i.e. those catalysts which have lost all or some of their catalytic activity. The present process is being described and exemplified with reference certain specific ionic liquid catalysts and processes catalyzed thereby, but such description is not intended to limit the scope of the invention. The methods described may be applied to other catalysts and processes by those persons having ordinary skill based on the teachings, descriptions and examples included herein.

The specific examples used herein refer to alkylation processes using ionic liquid systems, which are amine-based cationic species mixed with aluminum chloride. In such systems, to obtain the appropriate acidity suitable for the alkylation chemistry, the ionic liquid catalyst is generally prepared to full acidity strength by mixing one molar part of the appropriate ammonium chloride with two molar parts of aluminum chloride. The catalyst exemplified for the alkylation process is a 1-alkyl-pyridinium chloroaluminate, such as 1-butyl-pyridinium heptachloroaluminate.

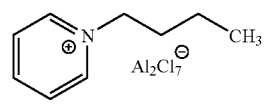

1-Butyl-pyridinium heptachloroaluminate

In general, a strongly acidic ionic liquid is necessary for paraffin alkylation, e.g. isoparaffin alkylation. In that case, aluminum chloride, which is a strong Lewis acid in a combination with a small concentration of a Broensted acid, is a preferred catalyst component in the ionic liquid catalyst scheme.

While not being bound to this or any other theory of operation, the present invention is based in part on our discovery that one of the major catalyst deactivation mechanisms is the formation of by-products known as conjunct polymers. The term conjunct polymer was first used by Pines and Ipatieff to distinguish these polymeric molecules from the usual polymers. Unlike typical polymers, conjunct polymers are poly-unsaturated cyclic, polycyclic and acyclic molecules formed by concurrent acid-catalyzed reactions including, among others, polymerization, alkylation, cyclization, and hydride transfer reactions. Conjunct polymers consist of unsaturated intricate network of molecules that may include one or a combination of 4-, 5-, 6- and 7-membered rings in their skeletons. Some examples of the likely polymeric species were reported by Miron et al. (*Journal of chemical and Engineering Data*, 1963) and Pines (*Chem. Tech*, 1982). These molecules contain double and conjugated double bonds in intricate structures containing a combination of cyclic and acyclic skeletons.

The conjunct polymers deactivate the chloroaluminate ionic liquid catalysts by weakening the acid strength of the catalyst through the formation of complexes of conjunct polymers and $AlCl_3$ possibly by means of electron-donor/electron-acceptor interactions. The conjunct polymers with their double bonds are the donors and the Lewis acid ($AlCl_3$) is the acceptor. Using their double bonds, the conjunct polymers coordinate to the Lewis acid ($AlCl_3$) in the ionic liquid and rendering the coordinated $AlCl_3$ for catalysis. Thus, the acidity of the catalyst becomes weaker and the overall catalytic activity becomes compromised and no longer effective for the intended purpose. Thus, the catalyst performance will become a function of the concentration of conjunct polymers in the ionic liquid phase. As more conjunct polymers accumulate in the ionic liquid phase the catalyst becomes less active. So, removal of all or a suitable portion of the conjunct polymers from the ionic liquid phase is a significant aspect of the present process for ionic liquids catalyst regeneration.

The term "conjunct polymer" as used herein also includes any other species which might complex to $AlCl_3$ by pi bonding or sigma bonding or other means, which results in those species binding to the ionic liquid, so they are not removable by simple hydrocarbon extraction.

The formation of conjunct polymers has also been observed in other acidic catalysts used in acid-catalyzed reactions, including HF, $H_2SO_4$ and $AlCl_3$ alkylations. Conjunct polymers are also called "red oils" due to their color and "acid-soluble oils" due to their high uptake in the catalyst phase where saturated hydrocarbons and paraffinic products are usually immiscible.

It is believed that deactivation of the catalyst by the presence of conjunct polymers is, in part at least, caused by coordination and complex formation between the Lewis acid $AlCl_3$ (electron pair acceptor) and the conjunct polymers (electron donors). In such complexes, the $AlCl_3$ is no longer available to act as a catalyst since it is tied-up in the $AlCl_3$-conjunct polymers complexes. It also appears that the presence (or accumulation) of conjunct polymer molecules in the catalyst phase is not by virtue of being miscible in the ionic liquid phase. While conjunct polymers may be somewhat miscible in the ionic liquids, their accumulation in the catalyst phase is more likely to being bound by strong acid-base interactions (complexation) rather than being soluble in the ionic liquid phase.

Conjunct polymers isolated from the catalyst phase by means of hydrolysis are highly soluble in hydrocarbons. However, attempts to remove them from the catalyst phase prior to hydrolysis by simple extraction methods with hydrocarbon solvents such as hexane, decane and toluene were unsuccessful. Other more polar solvents such as $CH_2Cl_2$ or chloroform may dissolve a chloroaluminate ionic liquid and therefore are not a selective solvent for dissolving and removing the conjunct polymers. Conjunct polymers may be isolated by hydrolysis. However, these methods of isolating the conjunct polymers are destructive, and result in an actual loss of a catalytic component ($AlCl_3$). The hydrolysis methods hydrolyze the catalytic component ($AlCl_3$) and transform it into inactive aluminum hydroxide and aluminum oxide. This indicates that the conjunct polymers are tightly held in the ionic liquid phase by fairly strong type of bonding system. Therefore, any successful attempt to reactivate and regenerate the catalyst must involve the removal of conjunct polymers to release aluminum trichloride from the $AlCl_3$— conjunct polymer complexes without destroying, consuming, or irreversibly tying up the $AlCl_3$.

In other words, one objective is to free the catalyst by replacing the conjunct polymers with other basic species that simply displace the polymer without destroying the catalyst or by suppressing the ability of conjunct polymers to form complexes with Lewis acids (aluminum chloride).

The deactivated catalyst can be revived in a nondestructive manner by freeing up the $AlCl_3$ from conjunct polymer-$AlCl_3$ complex. In principle, this can be accomplished by saturation of the double bonds of the conjunct polymers to eliminate their ability to coordinate to the Lewis acid ($AlCl_3$). By hydrogenation, the double bonds of the conjunct polymers will be saturated and no longer be able to be coordinated or complexed to $AlCl_3$. $AlCl_3$ no longer bound by conjunct polymers is then released to take part in catalytic reactions.

Among other things the present invention provides a process for the removal of the conjunct polymers from a used ionic liquid catalyst by saturating the double bonds of the conjunct polymers by means of hydrogenation thereby increasing the activity of the ionic liquid catalyst.

Hydrogenation is a well-established process both in the chemical and petroleum refining industries. Hydrogenation is conventionally carried out in the presence of a catalyst which usually comprises a metal hydrogenation component on a porous support material, such as a natural clay or a synthetic oxide. Nickel is often used as a hydrogenation component, as are noble metals such as platinum, palladium, rhodium and iridium. Typical support materials include kieselguhr, alumina, silica and silica-alumina. Depending upon the ease with which the feed may be hydrogenated, the hydrogen pressures used may vary from quite low to very high values, typically from about 100 to 2,500 psig.

The hydrogenation catalyst used in this invention may be any one of metallic or non-metallic catalysts which have hydrogenating ability. The preferred catalyst comprises at least one hydrogenation component selected from Group VI-B and VIII, present as metals, oxides, or sulfides. Specific examples of the metallic catalysts are Fe, Co, Ni, Ru, Rh, Pd, Ir, Os, Pt, Cr, Mn, Ti, V, Zr, Mo, and W. Specific examples of the non-metallic catalysts are Te and As. These metals or non-metals may be used singly or in combination.

Nobel metals such as palladium, platinum, or ruthenium, applied to diverse supports such as silicon dioxide, aluminum oxide, graphite, or activated charcoal, are well suited for the hydrogenation of organic and inorganic compounds. The hydrogenation component may also be supported on a refractory inorganic base, for example, alumina, silica, and composites of alumina-silica, alumina-boria, silica-alumina-magnesia, and silica-alumina-titania and materials obtained by adding zeolites and other complex oxides thereto. The refractory inorganic oxide is a material that has adequate mechanical strength and chemical stability at the reaction temperature of the catalyst.

The catalyst of the present invention can be manufactured by supporting catalytically active components on a catalyst carrier. The active components may be deposited on the surface of the catalyst carrier after the carrier has been formed, or they may be incorporated into the catalyst by being added to the carrier material during the formation of the catalyst carrier. Many such methods of preparation are known.

Hydrogenation may also be accomplished by using a metal or metal alloy hydrogenation catalyst. This hydrogenation catalyst may be any one of the various metallic catalysts which have hydrogenating ability. The preferred catalyst is selected from Group VI-B and VIII. Specific examples of the metallic catalysts are Fe, Co, Ni, Ru, Rh, Pd, Ir, Os, Pt, Cr, Mn, Ti, V, Zr, Mo, and W. These metals may be used singly, in combination or as alloys. Catalysts such as Raney nickel and alloys such as Ni/Al alloy may also be suitably employed.

The metals can be in the form of fine particles, granules, sponges, gauzes, etc. Each metal may be used in any number of forms: (1) macroscopic, which includes wires, foils, fine particles, sponges, gauzes, granules, etc.; and (2) microscopic, which includes powders, smokes, colloidal suspensions, and condensed metal films.

It is known that Raney-type-metal catalysts are prepared from alloys containing one or more catalytically 25 active metals (e.g., Ni, Co, Fe, Cu, Pd, etc.) and one or more catalytically inactive, easily dissolvable metals (e.g., Al, Si, Mg, Zn). The catalytically active metal component of the alloy is present in a so-called "dissolved" state, i.e. in a finely divided form. The inactive component is removed from the alloy by leaching the same with a solvent which does not attack the active metal. As solvents, generally aqueous alkaline solutions are used. During this procedure the active metal remains in the form of finely divided catalyst. The activity of the thus-obtained catalysts is higher than that of catalysts prepared, e.g., by reducing the appropriate metal oxides. This high activity explains the importance and the widespread use of such catalysts.

Hydrogenation may also be accomplished using a homogeneous hydrogenation catalyst. Numerous examples of such catalysts are disclosed in U.S. Pat. No. 5,334,791, which is incorporated by reference herein.

Homogeneous hydrogenation catalysts for the production of hydrogenation reactants are well known in the art, with many systems being based on rhodium metal combined with phosphine ligands. Examples of such catalysts were first described in J. A. Osborn, F. H. Jardine, J. F. Young and G. Wilkinson, J. Chem. Soc. (A) (1966) 1711. Other examples are soluble (homogenous) metal salts such as $PdCl_2$ and $NiCl_2$, and transition metal complexes such as $PdCl_2(triphenylphosphine)_2$ and $NiCl_2(triphenylphosphine)_2$. Other organic metal complexes, e.g., organometallic compounds of Ti, Ru, Rh, Zr, etc. are known to be useful homogeneous hydrogenation catalysts.

The Osborn et al. paper describes the hydrogenation of hydrogenatable products using a catalyst precursor of the formula $[RhCl(triphenylphosphine)_3]$ and a pressure of hydrogen gas of one atmosphere. U.S. Pat. No. 5,334,791 describes hydrogenation process for non-aromatic unsaturated hydrocarbons using catalyst precursors based on a group VIIIB transition metal and a phosphine ligand.

Also of note is the use of chiral bis tertiary diphosphines in asymmetric hydrogenation with rhodium(I) catalyst precursors. There are a number of patents related to synthesis and application of several rhodium-chiral diphosphine catalyst precursors: See for example, U.S. Pat. Nos. 3,419,907; 3,849, 490; 3,878,101; 4,166,824; 4,119,652; 4,397,787; 4,440,936.

Other homogeneous hydrogenation catalysts and their method of preparation are described in F. Albert Cotton and Geoffrey Wilkinson, "Advanced Inorganic Chemistry", Interscience Publishers, New York, 3rd Edition, 1972, pp 787 to 790.

Hydrogenation of use ionic liquid catalyst is shown by the following example. As noted previously, ionic liquid catalysts may become deactivated during use. For example, in an alkylate production unit, light ($C_2$-$C_5$) olefins and isoparaffin feeds are contacted in the presence of a catalyst that promotes the alkylation reaction. In one embodiment of a process in accordance with the present invention, this catalyst is a chloroaluminate ionic liquid. The reactor, which may be a stirred tank or other type of contactor (e.g., riser reactor), produces a biphasic mixture of alkylate hydrocarbons, unreacted isoparaffins, and ionic liquid catalyst containing some conjunct polymers. The dense catalyst/conjunct polymer phase may be separated from the hydrocarbons by gravity decanter. This catalyst will be partially deactivated by the conjunct polymers binding to $AlCl_3$. The recovered catalyst can be reactivated in a reaction system hydrogenation with a supported hydrogenation catalyst. The products of this step will be reactivated catalyst and hydrogenated conjunct polymers among others as described herein. The reactivated catalyst and the hydrogenated conjunct polymers can be separated, for example, by solvent washing, decantation, and filtration.

In one embodiment of the present invention using hydrogenation, a used ionic liquid catalyst/conjunct polymer mixture is introduced continuously into a regeneration reactor, which contains a fixed bed of a supported hydrogenation catalyst. Hydrogen gas and inert hydrocarbons in which hydrogenated conjunct polymers are soluble are fed into the reactor at the desired rate. The solvent may be a normal hydrocarbon ranging from $C_5$-$C_{15}$, preferably $C_5$-$C_8$. The residence time, temperature and pressure of the reactor will be selected to allow adequate hydrogenation of the conjunct polymers. The reaction product is withdrawn and sent to a separator. This mixture is then separated into three streams, one comprising hydrogen and light hydrocarbons, a second comprising inert hydrocarbons and saturated conjunct polymer and a third comprising regenerated ionic liquid catalyst. The denser and more viscous regenerated catalyst phase settles to the bottom and can be recovered by means of a gravity decanter. The reactivated ionic liquid catalyst is returned to the alkylation reactor. The solvent/conjunct polymer mix is separated by distillation to recover the solvent.

A metal and a Broensted acid are used for hydrogenation in another embodiment of the present invention, which is described using aluminum and HCl. Aluminum metal reacts with HCl to give hydrogen gas and $AlCl_3$. By introducing aluminum metal and HCl into ionic liquid catalysts deactivated by conjunct polymers, the hydrogen liberated can be used to saturate the conjunct polymer double bonds. Concurrently, fresh aluminum chloride is produced, which is the acid component in the chloroaluminate ionic liquid. This constitutes a two-function regeneration scheme for both hydrogenating the conjunct polymers to release the complexed $AlCl_3$ and producing fresh $AlCl_3$ which replenishes $AlCl_3$ that has been consumed or lost by other means during the reaction. The hydrogenated conjunct polymers can be removed by solvent extraction or decantation and the regenerated ionic liquid catalyst recovered by filtration. Our experiments have shown that this scheme is feasible and that the regenerated catalyst demonstrated equal or better activity for the alkylation of ethylene with isopentane compared with freshly prepared catalyst.

As seen from the prior description, an embodiment of a process according to the present invention utilizes hydrogenation to saturate the double bonds of conjunct polymers using aluminum metal and hydrochloric acid. Using aluminum metal and HCl will produce the needed hydrogen gas for the hydrogenation and will also produce fresh $AlCl_3$ that increases the acidity and the activity of the recycled catalyst by increasing the concentration of $AlCl_3$ in the ionic liquid to its upper limits. In some cases, the regenerated catalyst will be more active than the freshly prepared catalyst prior to being deactivated. The metal used in the regeneration process in accordance with the present invention is not limited to aluminum. Other electropositive metals will react with HCl to produce $H_2$ and the corresponding metal chloride can also be used. This includes sodium, lithium, zinc, iron, copper, magnesium, titanium, gallium and many others. Aluminum metal will be the metal of choice when chloroaluminate ionic liquids are used in the catalytic process to avoid contamination of the regenerated ionic liquid with metal chlorides other than $AlCl_3$. While some metal chlorides may work as co-catalyst, others may inhibit the alkylation mechanism and promote unwanted reaction pathway. The process is not limited to using HCl as the source of hydrogen. Other Broensted acids may also be used as a source of hydrogen including, but not limited to, HI, HBr, HF, $H_2SO_4$, $H_3PO_4$. In the case of chloroaluminate ionic liquids, hydro halides (HI, HCl, HBr, HF) will be the acids of choice. Among the hydro halides hydrochloric acid is preferred to avoid introduction of conjugate bases other than halides and preferably other than chlorides.

As shown in the Examples, the conjunct polymers are removed by hydrogenation using aluminum and hydrogen chloride. Adding aluminum and hydrogen chloride to used ionic liquid catalyst and stirring the resulting mixture (in autoclave) at room temperature or at 50° C. at the autogenic pressure led to removal of >90% of the conjunct polymers as hydrogenated hydrocarbons. The hydrogenated conjunct polymers (immiscible in the ionic liquid phase) were removed by simple extraction methods with other hydrocarbons (such as hexanes) or by means of decantation. The regenerated ionic liquid catalyst was removed from the remaining mixture (freshly made $AlCl_3$ and aluminum metal) by filtration.

The recovered regenerated ionic liquid catalyst was tested for activity by alkylating ethylene with isopentane and the regenerated catalyst showed better activity than both the deactivated catalyst and the fresh catalyst from which the deactivated catalyst was made. The selectivity of the regenerated catalyst was identical to the selectivity of the freshly-made catalyst.

In an alkylate production unit, light ($C_2$-$C_5$) olefins and isoparaffin feeds are contacted in the presence of a catalyst that promotes the alkylation reaction. In one embodiment of a process in accordance with the present invention, this catalyst is a chloroaluminate ionic liquid. The reactor, which may be a stirred tank or other type of contactor (e.g., riser reactor), produces a biphasic mixture of alkylate hydrocarbons, unreacted isoparaffins, and ionic liquid catalyst containing some conjunct polymers. The catalyst/conjunct polymer phase may be separated from the hydrocarbons by means of a gravity decanter. This catalyst will be partially deactivated by the conjunct polymers binding to $AlCl_3$. The recovered catalyst can be reactivated in a reaction system employing aluminum metal and HCl. The products of this step will be reactivated catalyst and hydrogenated conjunct polymers. These can be separated by solvent washing, decantation, and filtration.

It is not necessary to regenerate the entire charge of catalyst. In some instances only a portion or slipstream of the catalyst charge is regenerated. In those instances only as much ionic liquid catalyst is regenerated as is necessary to maintain a desired level of catalyst activity in the process in which the ionic liquid is used as the catalyst.

In one embodiment of the present invention with reference to the FIGURE, the ionic liquid catalyst/conjunct polymer mixture is introduced continuously into a stirred tank reactor (CSTR), where aluminum metal powder is added by way of a screw-type feeder. The aluminum is kept under inert gas (nitrogen or other) to prevent oxidation. HCl gas is fed in at the desired rate to produce $H_2$ gas and $AlCl_3$. The residence time of the reactor will be selected to allow adequate hydrogenation of the conjunct polymers. The reaction product is withdrawn and mixed with a hydrocarbon solvent (e.g., hexane) in which the hydrogenated conjunct polymers are soluble. The solvent may be a normal hydrocarbon ranging from $C_5$-$C_{15}$; preferably $C_5$-$C_8$. This mixture is then separated in a gravity decanter, from which the dense ionic liquid phase is withdrawn. Unreacted aluminum in the ionic liquid phase is removed by filtration. The reactivated ionic liquid catalyst is returned to the alkylation reactor. The solvent/conjunct polymer mix is separated by distillation to recover the solvent.

Hydrogenation conditions for all types of hydrogenation described herein will generally include temperatures of −20° C.-200° C., preferably 50°-150° C., pressures of atmospheric-5000 psig, preferably 50-500 psig, and a contact time of 0.1 minute-24 hours, and preferably from ½-2 hours in a normal hydrocarbon as a solvent.

In another embodiment of the present invention, an acidic catalyst is regenerated by adding a basic reagent which breaks up $AlCl_3$-conjunct polymer complexes.

There are numerous reagents that can be used to break up the $AlCl_3$-conjunct polymer complexes including, e.g. amines. One important consideration is that any of these basic species would form, most likely, irreversible complexes with $AlCl_3$ similar to the $AlCl_3$-conjunct polymer complexes. Moreover, there is no selective method to break up $AlCl_3$-conjunct polymer complexes. In other words, any reagent that may be used to break up the $AlCl_3$-conjunct polymer complexes will also react with other aluminum species in the catalyst phase Therefore, to ensure the complete break-up of the complexes by a reagent, sufficient reagent must be added to react with all $AlCl_3$ molecules in the system, both bound and unbound.

Since any reagent to be used in the removal process of conjunct polymers from the spent catalyst will form new complexes (e.g. AlCl$_3$-reagent complexes), thereby destroying active catalytic components, there will be no gain from this procedure unless the reagent to be used is part of the catalyst system undergoing regeneration. Consequently, a process according to this invention, employs basic species that can displace the conjunct polymers and be part of the regeneration or recycling process of the catalyst. For example, in the butyl-pyridinium chloroaluminate ionic liquid catalyst system, butylpyridinium chloride, where the chloride is the basic specie, would be used to break up the AlCl$_3$-conjunct polymer complexes in the spent catalyst.

Where, for example, the ionic liquid is formed by mixing either an amine hydrochloride or an alkyl ammonium halide with a Lewis acid, in accordance with the present invention, a process whereby aluminum chloride is released from the AlCl$_3$-conjunct polymer complex is conducted by using either amines or ammonium chloride depending on the ionic liquid that is being regenerated. More specifically, for 1-butyl-pyridinium heptachloroaluminate, the conjunct polymers are released by adding butyl-pyridinium chloride to the deactivated catalyst. The chloride of the 1-butyl-pyridinium chloride interacts with the non-complexed and complexed aluminum species in the spent catalyst phase and thus freeing the conjunct polymers from the AlCl$_3$-conjunct polymer complexes. The released conjunct polymers are then removed, for example, by extraction with low boiling n-paraffins. The remaining solid residues, presumably butylpyridinium tetrachloroaluminate, are converted back to ionic liquid (butylpyridinium heptachloroaluminate) by adding more AlCl$_3$ as set forth below.

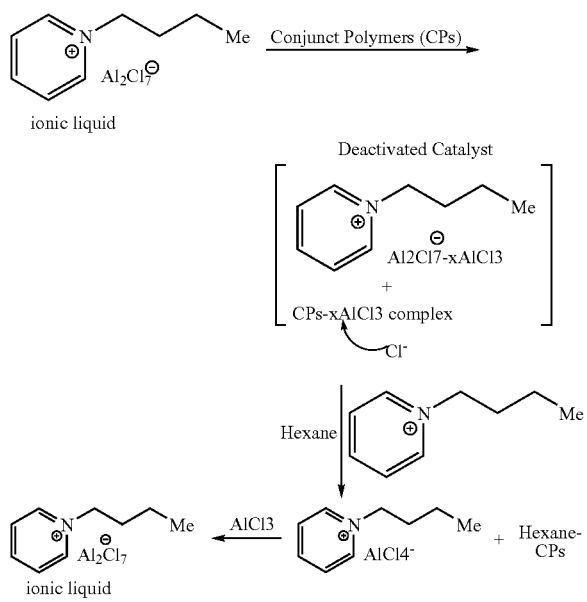

Using this process, a stream of the catalyst is reactivated and the regenerated catalyst is recycled back into the reactor. By employing a method according to the invention, the concentration of the conjunct polymers can be minimized while the catalyst strength is maintained by reintroducing the regenerated catalyst into the reaction cycle.

The principle used for selecting a suitable reagent is not only limited to using butylpyridinium in butylpyridinium chloroaluminate or butylpyridinium chloroaluminate-like ionic liquids. It is applicable to ionic liquids in general. The reagent is one which corresponds to the basic parent species of cation from which the ionic liquid to be regenerated was originally produced.

As a further example of this principle, consider ionic liquids that were produced from ammonium hydrohalides and aluminum chlorides. In this case, the basic reagent that is used to break up the AlCl$_3$-conjunct polymer complex is the free amine corresponding to the ammonium hydrohalide salt. Conjunct polymers are removed and ammonium tetrachloroaluminate is produced. Addition AlCl$_3$/HCl is used to re-constitute the ionic liquid.

In summary, for aluminum chloride-based ionic liquid catalysts, a deactivated catalyst can be revived in a nondestructive manner by freeing up the AlCl$_3$ from conjunct polymer-AlCl$_3$ complex. The process employs the parent amine in the case of an ionic liquid catalyst derived from ammonium hydrochlorides and aluminum halides, or employing alkyl ammonium halides when the ionic liquid catalyst is derived from alkyl ammonium halides and aluminum.

Addition of a basic reagent is shown by the following example. In an alkylate production unit, light (C$_2$-C$_5$) olefins and isoparaffin feeds are contacted in the presence of a catalyst that promotes the alkylation reaction. In one embodiment of a process in accordance with the present invention, this catalyst is a chloroaluminate ionic liquid. The reactor, which may be a stirred tank or other type of contactor (e.g., riser reactor), produces a biphasic mixture of alkylate hydrocarbons, unreacted isoparaffins, and ionic liquid catalyst containing some conjunct polymers. The catalyst/conjunct polymer phase, which is denser than other components, may be separated from the hydrocarbons by means of a gravity decanter. This catalyst will be partially deactivated by the conjunct polymers binding to AlCl$_3$. The recovered catalyst can be reactivated by first contacting the recovered catalyst with butylpyridinium chloride in a first regeneration reactor to give butylpyridinium tetrachloroaluminate and "free" conjunct polymer. The free conjunct polymer is removed. The remaining butylpyridinium tetrachloroaluminate is then sent to a second regeneration reactor where it is contacted with AlCl$_3$ to fully restore the activity of the catalyst. The regenerated ionic liquid catalyst effluent of the second reactor is then recycled to the alkylate production unit.

In one embodiment of the present invention using the addition of a basic reagent, a used ionic liquid catalyst/conjunct polymer mixture is introduced continuously into a regeneration reactor along with butylpyridinium chloride and inert hydrocarbons in which hydrogenated conjunct polymers are soluble at the desired rate. The inert hydrocarbons may be a normal hydrocarbons ranging from C$_5$-C$_{15}$, preferably C$_5$-C$_8$ and their mixtures, although other hydrocarbons may be employed. A conjunct polymer-hydrocarbon mixture is removed from the first regeneration reactor. The remaining butylpyridinium tetrachloroaluminate is then sent to a second regeneration reactor where it is contacted with AlCl$_3$ to fully restore the activity of the catalyst. The regenerated ionic liquid catalyst is removed from the second reactor and can then be recycled.

Another method of regenerating a used acidic catalyst in accordance with the present invention by reaction with an isoparaffin in the presence of a Broensted acid, e.g. HCl. While not being bound to any theory, we believe that reaction of isobutane with the double bonds in the conjunct polymers leads to a partial or complete "capping" (alkylating) of the conjunct polymers double bonds disrupting their ability to complex to, e.g., aluminum trichloride. This is supported by our discovery that olefin oligomers can be terminated and saturated by carrying out the chloroaluminate ionic liquid catalyzed oligomerization reaction in the presence of isobutane.

In a process according to the present invention an isoparaffin feedstock is used to reactivate a used acidic ionic liquid catalyst. The simplest isoparaffin is isobutane. Isopentanes, isohexanes, isopentanes, and other higher isoparaffins may also be useable in the process of the present invention. Mixtures of light isoparaffins can also be used in the present invention. Mixtures such as $C_4$-$C_5$ isoparaffins can be used and may be advantageous because of reduced separation costs. The isoparaffin feedstock may also contain diluents such as normal paraffins. This can be a cost savings by reducing the cost of separating isoparaffins from close boiling paraffins. Normal paraffins will tend to be unreactive diluents in the process of the present invention.

A preferred isoparaffin is one which has a tertiary carbon atom, i.e., one which is substituted by three alkyl groups and has one remaining hydrogen, and therefore is capable of participating in hydride transfer reactions.

Broensted acids other than HCl may also be used in this embodiment including, but not limited to, HI, HBr, HF, $H_2SO_4$, $H_3PO_4$. In the case of chloroaluminate ionic liquids, hydrohalides (HI, HCl, HBr and HF) will be the acids of choice. Among the hydrohalides, hydrochloric acid is preferred. Other strong acids that are proton donors may also be suitably used.

In one example of this embodiment, the ionic liquid catalyst/conjunct polymer mixture is introduced continuously into a reactor. HCl gas and isobutane are fed in to the reactor at the desired rate. The residence time of the reactor will be selected to allow adequate alkylation of the conjunct polymers. The reaction product is withdrawn and mixed with a hydrocarbon solvent (e.g., hexane) in which the released conjunct polymers are soluble. The solvent may be normal hydrocarbons ranging from $C_5$-$C_{15}$; preferably $C_5$-$C_8$. This mixture is then separated in a gravity decanter, from which the denser ionic liquid phase is withdrawn. The reactivated ionic liquid catalyst is returned to the alkylation reactor. The solvent/conjunct polymer mix is separated by distillation to recover the solvent.

Typical alkylation reaction conditions generally may include a temperature of from −10° C. to +150° C., a pressure of from 0 psig to 3500 psig, an isopentane to conjunct polymer molar ratio of from 0.5 to 25 or more and a residence time of 0.5 min to 1 hour or longer It is not necessary in any of the methods in accordance with the invention to regenerate the entire charge of catalyst. In some instances only a portion or slipstream of the catalyst charge is regenerated. In those instances only as much ionic liquid catalyst is regenerated as is necessary to maintain a desired level of catalyst activity in the process in which the ionic liquid is used as the catalyst.

The block diagram in the FIGURE is not meant to restrict the present invention any sort or type of reactor. Also, the FIGURE shows an inert hydrocarbon entering the reactor together with the deactivated ionic liquid. That is an optional implementation. The hydrocarbon could be left out entirely or it could be added to the separator to allow extraction and separation simultaneously. Other modifications are possible and are included in the scope of the present invention.

The following Examples are illustrative of the present invention, but are not intended to limit the invention in any way beyond what is contained in the claims which follow.

EXAMPLES

Example 1

Preparation of Fresh 1-Butylpyridinium Chloroaluminate Ionic Liquid Catalyst A (Fresh IL A)

1-butyl-pyridinium chloroaluminate is a room temperature ionic liquid prepared by mixing neat 1-butyl-pyridinium chloride (a solid) with neat solid aluminum trichloride in an inert atmosphere. The syntheses of butylpyridinium chloride and the corresponding 1-butyl-pyridinium chloroaluminate are described below. In a 2-L Teflon-lined autoclave, 400 gm (5.05 mol.) anhydrous pyridine (99.9% pure purchased from Aldrich) were mixed with 650 gm (7 mol.) 1-chlorobutane (99.5% pure purchased from Aldrich). The autoclave was sealed and the neat mixture allowed to stir at 125° C. under autogenic pressure over night. After cooling off the autoclave and venting it, the reaction mix was diluted and dissolved in chloroform and transferred to a three liter round bottom flask. Concentration of the reaction mixture at reduced pressure on a rotary evaporator (in a hot water bath) to remove excess chloride, un-reacted pyridine and the chloroform solvent gave a tan solid product. Purification of the product was done by dissolving the obtained solids in hot acetone and precipitating the pure product through cooling and addition of diethyl ether. Filtering and drying under vacuum and heat on a rotary evaporator gave 750 gm (88% yields) of the desired product as an off-white shiny solid. $^1$H-NMR and $^{13}$C-NMR were consistent with the desired 1-butyl-pyridinium chloride and no impurities were observed.

1-butylpyridinium chloroaluminate was prepared by slowly mixing dried 1-butylpyridinium chloride and anhydrous aluminum chloride ($AlCl_3$) according to the following procedure. The 1-butylpyridinium chloride (prepared as described above) was dried under vacuum at 80° C. for 48 hours to get rid of residual water (1-butylpyridinium chloride is hydroscopic and readily absorbs water from exposure to air). Five hundred grams (2.91 mol.) of the dried butylpyridinium chloride were transferred to a 2-Liter beaker in a nitrogen atmosphere in a glove box. Then, 777.4 gm (5.83 mol.) of anhydrous powdered $AlCl_3$ (99.99% from Aldrich) were added in small portions (while stirring) to control the temperature of the highly exothermic reaction. Once all the $AlCl_3$ was added, the resulting amber-looking liquid was left to gently stir overnight in the glove box. The liquid was then filtered to remove any un-dissolved $AlCl_3$. The resulting acidic 1-butyl-pyridinium chloroaluminate was used as the catalyst for the alkylation of isopentane with ethylene.

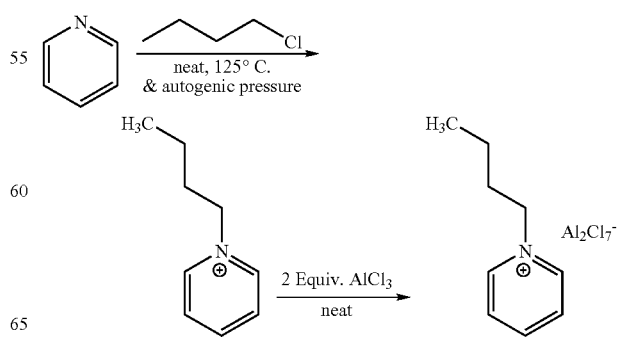

Example 2

Preparation of "Deactivated" 1-Butylpyridinium Chloroaluminate Ionic Liquid Catalyst (Deactivated Catalyst A)

"Deactivated" or "used" 1-butylpyridinium chloroaluminate ionic liquid catalyst was prepared from "fresh" 1-butylpyridinium chloroaluminate ionic liquid catalyst by carrying out the isobutane alkylation reaction in a continuous flow microunit under catalyst recycle with accelerated fouling conditions.

The microunit consists of feed pumps for isobutane and butenes, a stirred autoclave reactor, a back pressure regulator, a three phase separator, and a third pump to recycle the separated ionic liquid catalyst back to the reactor. The reactor was operated at 80 to 100 psig pressure and with cooling to maintain a reaction temperature of ~10° C. To start the reaction, isobutane, butenes, and HCl were pumped into the autoclave at the desired molar ratio (isobutane/butenes >1.0), through the back pressure regulator, and into the three phase separator. At the same time, fresh chloroaluminate ionic liquid catalyst was pumped into the reactor at a rate pre-calculated to give the desired catalyst/feed ratio on a volumetric basis. As the reaction proceeded, ionic liquid separated from the reactor effluent and collected in the bottom of the three phase separator. When a sufficient level of catalyst built up in the bottom of the separator, the flow of fresh ionic liquid was stopped and catalyst recycle from the bottom of the separator was started. In this way, the initial catalyst charge was continually used and recycled in the process.

The following process conditions were used to generate Deactivated Catalyst A (1-butylpyridinium chloroaluminate ionic liquid catalyst) from Fresh Catalyst A:

| Process Variable | | |
|---|---|---|
| Isobutane pump rate | 4.6 | g/min |
| Butene pump rate | 2.2 | g/min |
| IL Catalyst pump rate | 1.6 | g/min |
| HCl flow rate | 3.0 | SCCM |
| pressure | 100 | psig |
| temperature | 10 | ° C. |

The reaction was continued for 72 hours when it was judged that the catalyst had become sufficiently deactivated.

Example 3

Determination of the Amounts of Conjunct Polymer and Olefin Oligomers in Deactivated IL A The wt % of conjunct polymers in the spent (deactivated) ionic liquid was determined by hydrolysis of known weights of the spent catalyst. The example below is a typical procedure for measuring conjunct polymers in a given spent catalyst. In a glove box, 15 gm of a spent ionic liquid catalyst in a flask were rinsed first with 30-50 ml of anhydrous hexane to remove (from the spent catalyst) any residual hydrocarbon or olefinic oligomers. The hexane rinse was concentrated under reduced pressure to give only 0.02 gm of yellow oil (0.13%). Then, 50 ml of anhydrous hexane was added to the rinsed catalyst followed by slow addition of 15 ml of water, and the mixture was stirred at 0° C. for 15-20 minutes. The resulting mixture was diluted with additional 30 ml hexanes and stirred well for additional 5-10 minutes. The mixture was allowed to settle down to two layers solution and some solid residue. The organic layer was recovered by decanting. The aqueous layer was further washed with additional 50 ml hexanes. The hexanes layers were combined and dried over anhydrous $MgSO_4$, filtered and concentrated to give 2.5 gm (16.7 wt % of the spent catalyst) of viscous dark orange-reddish oil. It was determined therefore that this particular spent catalyst contains 0.13% oligomers and 16.7% conjunct polymers. The hydrolysis can also be accomplished using acidic (aqueous HCl) or basic (aqueous NaOH) solutions.

Example 4

Characterization of Recovered Conjunct Polymer from Deactivated IL A

The recovered conjunct polymers according to the procedure described in Example 3 were characterized by elemental analysis and by infrared, NMR, GC-Mass and UV and spectroscopy methods. The recovered conjunct polymers have hydrogen/carbon ratio of 1.76 and chlorine content of 0.8%. $^1$H-NMR and $^{13}$C-NMR showed the presence of olefinic protons and olefinic carbons. Infra Red indicated the presence of olefinic regions and the presence of cyclic systems and substituted double bonds. GCMS showed the conjunct polymers to have molecular weights ranging from 150-mid 600 s. The recovered conjunct polymers have boiling ranges of 350-1100° F. as indicated by high boiling simulated distillation analysis. UV spectroscopy showed a UV $\lambda_{max}$ at 250 nm pointing highly conjugated double bonds systems.

Example 5

Hydrogenation of Deactivated IL A Using Al Metal and HCl and Determination of the Amount of Residual Conjunct Polymers Saturation of the double bonds of the conjunct polymers using aluminum metal and HCl was achieved according to the procedure shown below. To 40 gm of spent ionic liquid containing 15.5 wt % (6.2 gm) of conjunct polymers in 300 cc autoclave, 100 ml of anhydrous n-hexane and 9 gm of aluminum were added. The autoclave was sealed (all done in glove box), and 10 gm of anhydrous HCl were introduced via an inlet. The reaction was stirred at >1200 rpm and with intent of heating to 75° C. The reaction was very exothermic and after few minutes the temperature rose to 81° C. and the pressure to 290 psi. Then, the pressure and the temperature began to drop. At the end of the run (1.5 hrs) the temperature was at 75° C. and the pressure was at 99 psi. The reactor was cooled to room temperature and the organic phase was decanted off. The ionic liquid phase was rinsed twice with 50 ml anhydrous hexane. The hexane layers were combined and concentrated under reduced pressure and heat to remove the solvent (hexane) giving 5.8 gm (93.5% of the weight of conjunct polymer originally present in the deactivated ionic liquid.). Hydrolysis of 10 gm of the treated ionic liquid gave 0.06 gm of conjunct polymers indicating a total of 4% remained in the ionic liquid phase. The hydrogenated products showed normal H/C ratios and NMR, IR and UV spectroscopy all indicated the disappearance of the double bonds.

Example 6

Determination of Activity of Deactivated IL A Using Batch Alkylation of isoPentane with Ethylene The regenerated catalyst was highly active. The activity of the regenerated ionic liquid catalyst matched the activity of the freshly prepared catalyst in the alkylation of ethylene with isopentane to make $C_7$s. Table 1 compares the activity of the regenerated catalyst with the freshly prepared and the spent catalysts in the alkylation of ethylene with isopentane. The alkylation of isopentane with ethylene was done according to the procedure describe below. A 300 cc autoclave was charged with 20 gm of ionic liquid catalyst, 100 gm anhydrous isopentane, 10 gm ethylene and 0.3 gm anhydrous HCl. The reaction was then stirred ~1200 rpm and heated to 50° C. at autogenic pressures. The starting pressure was usually 280-320 psi. The reaction was usually complete when the pressure dropped down to single digits. In the case of slow going reaction, the reaction was allowed to go on for 1 hr. At the end of the reaction, the reactor was vented out and a gas sample was checked by GC for ethylene concentration. The liquid reaction mixture was allowed to settle into 2 phases. The organic phase was decanted and analyzed for product distribution by GC analysis. The following Table 1 draws a comparison among the freshly made, the spent and the regenerated catalysts.

TABLE 1

|  | Fresh Catalyst | Spent Catalyst | Regenerated. Catalyst |
| --- | --- | --- | --- |
| Reaction Time | 9 min. | 60 min. | 6 min. |
| Starting Pressure | 300 psi | 286 psi | 297 psi |
| Ending pressure | 11 | 302 psi | 7 |
| iC5 | 72 | 98% | 67 |
| C7s | 19 | ~1.4% | 19 |
| 2,3-DM-Pentane | 8.23 | 0.9 | 9 |
| 2,4-DM-Pentane | 10 | 0.6 | 10 |
| 2,3DM/2,4DM | 0.82 | 1.5 | 0.9 |

Example 7

Removal of Conjunct Polymer from Deactivated Catalyst A by the Addition of Pyridine Note that a process based on this example would require the addition of HCl and $AlCl_3$ in the second regeneration reactor. In this case, the cation of the ionic liquid is pyridinium hydrochloride chloride, with H— instead of butyl-.

Deactivated Catalyst A (10.022 g) containing 24.6% conjunct polymers was weighed into a bottle and treated with 2.24 g of pyridine. After stirring for 45 minutes at ambient temperature, the contents of the bottle were extracted three times with 6.8 g of hexane. The hexane extracts were combined and evaporated under a stream of nitrogen. The net weight of residue was 1.84 grams or 18.4 wt %. The starting spent ionic liquid contained 24.6% conjunct polymers.

Example 8

Removal of Conjunct Polymer from Deactivated Catalyst A by 1-Butyl-Pyridinium Chloride In a round bottom reaction flask equipped with stirring bar and drying tube ($CaCl_2$ drying tube) 100 gm of anhydrous hexane were added to 20 gm of spent butylpyridinium chloroaluminate ionic liquid catalyst containing 16 wt % (3.2 gm) conjunct polymers. Five grams of butylpyridinium chloride was added to the 20 gm of spent catalyst already in 100 ml anhydrous hexane. The reaction was stirred for 30 min. and the hexane layer was decanted off. The residue was rinsed with an additional 50 ml hexane. The hexane layers were added and concentrated to give 1.2 gm of possible 3.2 gm of conjunct polymers. An additional 3 gm of butylpyridinium chloride and 50 ml anhydrous hexane were added to the ionic liquid residue from the treatment of the first 5 gm of butylpyridinium chloride and the mixture was stirred for ~15-20 minutes. The reaction mixture turned into two phases. One phase consisted of granulated brown solids and the hexane layer containing the remainder of the conjunct polymers. The hexane layer was decanted off and the remaining solids were rinsed with additional 50 ml anhydrous hexane. The hexane layers were combined and concentrated on a rotary evaporator to give additional 1.95 gm of conjunct polymers (in addition to the 1.2 gm recovered from the first addition of butylpyridinium chloride). Thus, a total of 3.15 gm or 98.4% of the conjunct polymers present in the spent catalyst were removed. The above procedure was repeated with similar results using other spent catalysts with varying conjunct polymers contents.

The recovered conjunct polymers removed by the procedure described above exhibited all the physical and spectroscopic characteristics of conjunct polymers isolated by hydrolysis methods.

The recovered solid were stripped off the solvent (not to dryness) on a rotary evaporator at 14 torr and 60° C. To the obtained brown solids, in an Erlenmeyer flask in a glove box, 6.5 gm of $AlCl_3$ were slowly added while stirring. After al the $AlCl_3$ was added, the resulting liquid was allowed to stir for additional 30 minutes. The liquid was then filtered and used for alkylation of ethylene with isopentane as a test for the activity of this partially regenerated ionic liquid catalyst.

Example 9

Determination of the Activity of the Regenerated ButylPyridinium Chloroaluminate Ionic Liquid Catalyst The regenerated butylpyridinium chloroaluminate ionic liquid catalyst described in Example 8 was tested for activity by using it as the catalyst in the alkylation of isopentane with ethylene and comparing it with freshly-made catalyst. The alkylation of isopentane with ethylene was done according to the following procedure. A 300 cc autoclave was charged with 20 gm of ionic liquid catalyst, 100 gm anhydrous isopentane, 10 gm ethylene and 0.3 gm anhydrous HCl. The reaction was then stirred ~1200 rpm and heated to 50° C. at autogenic pressures. The starting pressure was usually 280-320 psi. The reaction was usually complete when the pressure dropped down to single digits. In the case of slow going reaction, the reaction was allowed to go on for 1 hr. At the end of the reaction, the reactor was vented out and a gas sample was checked by GC for ethylene concentration. The two phase reaction mixture was allowed to settle into catalyst phase (lower phase) and the hydrocarbon phase (the upper phase). The hydrocarbon phase containing the feeds and the alkylation products was decanted and analyzed for product distribution by GC analysis.

Table 2 below shows the ethylene/isopentane alkylation results of this regenerated catalyst compared with the alkylation results of the fresh and the spent catalyst.

TABLE 2

|  | Fresh Catalyst | Spent Catalyst | Regen. Cat. |
| --- | --- | --- | --- |
| Reaction Time | 9 min. | 60 min. | 14 min. |
| Starting Pressure | 300 psi | 286 psi | 280 psi |
| Ending pressure | 17 | 302 psi | 4 psi |

TABLE 2-continued

|  | Fresh Catalyst | Spent Catalyst | Regen. Cat. |
|---|---|---|---|
| iC5 | 72 | 98% | 69.4% |
| C7s | 19 (72%) | ~1.4% | 20.1% |
| 2,3-DM-Pentane | 8.23 (31.5%) | 0.9 | 10.7% |
| 2,4-DM-Pentane | 10 (38%) | 0.6 | 8.9% |
| 2,3DM/2,4DM | 0.82 | 1.5 | 1.2 |

Alkylation of ethylene with isopentane at iC5/C2⁻ of 4 @ 50° C.

From the table above, the activity of the regenerated catalyst is comparable to that of the fresh catalyst. The spent catalyst containing the conjunct polymers is inactive.

Example 10

Removal of Conjunct Polymers from Deactivated Catalyst A by Hydrogenation with Palladium on Carbon Catalyst In a drybox, 3.0 grams of 10% palladium on carbon (Pd/C) catalyst was charged to a 100 mL stirred autoclave. Next, ~30 mL (31.33 g) of Deactivated Catalyst A was added. The autoclave was taken out of the drybox and charged with 900 psig hydrogen at ambient temperature. The reactor was heated to 100° C. for 14.75 hours and then cooled. A portion of the recovered catalyst (22.48 g) was extracted three times with 7 g of dry hexane. The hexane extracts were combined and evaporated under a stream of nitrogen to yield 0.408 g of clear, colorless oil. This corresponds to a recovery of 9.9 wt % of the conjunct polymer originally present in the Deactivated Catalyst A.

An 11.26 g sample of hexane-extracted, hydrogenated Deactivated Catalyst A was weighed into a bottle and hydrolyzed as described in Example 3. After combining the hexane extracts and evaporation under a stream of nitrogen, 0.87 g of a non-volatile residue was recovered. This corresponds to 7.73 wt % conjunct polymer remaining on the Deactivated Catalyst A after hydrogenation with 10% Pd/C catalyst. This corresponds to removal of 37.2 wt % of the conjunct polymer originally present in Deactivated Catalyst A. The difference between 9.9% hydrogenated conjunct polymer recovered and 37.2% conjunct polymer removed from Deactivated Catalyst A is due to losses during hexane evaporation of light components formed by hydrocracking.

Example 11

Removal of Conjunct Polymer from Deactivated Catalyst B by Hydrogenation with Palladium on Carbon Catalyst The procedure of Example 10 was repeated using Deactivated Catalyst B (31.33 g). The amount of 10% Pd/C catalyst was 0.10 g. Hexane, 30 mL, was also added to aid stirring. The initial pressure at ambient temperature was 900 psig. After heating 18 hours at 100° C. and cooling, the pressure was 650 psig. After extraction of hexane and evaporation of light components, 0.43 g of clear, colorless, oil was recovered. This corresponds to a recovery (as hydrogenated conjunct polymer) of 5.92 wt % of the original conjunct polymer present in Deactivated Catalyst B.

A sample of 15.009 g of Deactivated Catalyst B after hydrogenation and hexane extraction was placed in a bottle and hydrolyzed as described in Example 3. After hexane extraction and evaporation of the volatiles from the combined hexane extracts, a residue of 1.56 g of conjunct polymer was obtained. This corresponds to conjunct polymers content after hydrogenation of 10.4 wt %. Alternatively, 61.6 wt % of the conjunct polymer originally present in Deactivated Catalyst B was removed by hydrogenation.

Example 12

Removal of Conjunct Polymer from Deactivated Catalyst C by Hydrogenation with Palladium on Alumina Catalyst The procedure of Example 10 was repeated using Deactivated Catalyst C (21.278 g). The hydrogenation catalyst was 1.04 g of 1.0 wt % Pd on $Al_2O_3$. In this experiment, no hexane was added to aid stirring. The initial pressure at 100° C. was ~1212 psig and after heating 4.5 hours at 100° C., the pressure was ~1090 psig. After extraction of hexane and evaporation of light components, no oil was recovered.

A sample of 17.33 g of Deactivated Catalyst C after hydrogenation and hexane extraction was placed in a bottle and hydrolyzed as described in Example 3. After hexane extraction and evaporation of the volatiles from the combined hexane extracts, a residue of 1.49 g of conjunct polymer was obtained. This corresponds to conjunct polymer content after hydrogenation of 8.60 wt %. Alternatively, 37.4 wt % of the conjunct polymer originally present in Deactivated Catalyst C was removed by hydrogenation.

Example 13

Removal of Conjunct Polymer from Deactivated Catalyst C by Hydrogenation with Supported Platinum on Alumina Catalyst The procedure of Example 10 was repeated using Deactivated Catalyst C (20.78 g). The hydrogenation catalyst was 1.46 g of 0.5 wt % Pt on $Al_2O_3$. In this experiment, no hexane was added to aid stirring. The initial pressure at 100° C. was ~1250 psig and after heating 4.5 hours at 100° C., the pressure was ~1190 psig. After extraction of hexane and evaporation of light components, no oil was recovered.

A sample of 17.55 g of Deactivated Catalyst C after hydrogenation and hexane extraction was placed in a bottle and hydrolyzed as described in Example 3. After hexane extraction and evaporation of the volatiles from the combined hexane extracts, a residue of 2.18 g of conjunct polymer was obtained. This corresponds to a conjunct polymer content after hydrogenation of 12.4 wt %. Alternatively, 9.7 wt % of the conjunct polymer originally present in Deactivated Catalyst C was removed by hydrogenation.

Example 14

Removal of Conjunct Polymer from Deactivated Catalyst C by Hydrogenation with Supported Ni Catalyst The procedure of Example 10 was repeated using Deactivated Catalyst C (19.20 g). The hydrogenation catalyst was 1.02 g of Ni on synthetic mica montmorillonite. The hydrogenation catalyst had been previously reduced in flowing hydrogen at ambient pressure and at 450° C. In this experiment, no hexane was added to aid stirring. The initial pressure at 100° C. was ~1250 psig and after heating 4 hours at 100° C., the pressure was ~1200 psig. After extraction of hexane and evaporation of light components, no oil was recovered.

A sample of 15.76 g of Deactivated Catalyst C after hydrogenation and hexane extraction was placed in a bottle and hydrolyzed as described in Example 3. After hexane extraction and evaporation of the volatiles from the combined hexane extracts, a residue of 1.82 g of conjunct polymer was obtained. This corresponds to conjunct polymer content after hydrogenation of 11.6 wt %. Alternatively, 16.0 wt % of the conjunct polymer originally present in Deactivated Catalyst C was removed by hydrogenation.

Example 15

Removal of Conjunct Polymer from Deactivated Catalyst A by Hydrogenation over Ni—Al Alloy As a way for regenerating deactivated chloroaluminate ionic liquids, 35 gm of spent ionic liquids containing 22.3 wt % (7.8 gm) conjunct polymers in a 300 cc autoclave, 2 gm of Ni—Al alloy and 70 ml of anhydrous hexane were added. The autoclave was sealed and pressurized with hydrogen to 500 psi and heated to 100° C. while stirring at >1200 rpm for ~1.5 hrs. The starting pressure was 500 psig at room temperature. As the autoclave heated up, the pressure rose to 620 psig. As the reaction continued, pressure dropped to 560 psig and remained at that pressure for the remainder of the reaction time. The reactor was cooled down and to the contents allowed to settle. The resultant reaction mixture contained the hexane layer (the top layer), the ionic liquid layer (the bottom layer) and the Ni—Al alloy settled to the bottom of the reactor. The hexane layer was decanted off and saved. The ionic liquid layer was rinsed 3×50 ml anhydrous hexane. The hexane from the reaction and all hexane rinses were combined and dried over MgSO4. Filtration and concentration of the hexane under reduced pressure (~24 torr) in a hot water bath (~75° C.) gave 6.9 gm of slightly faint yellow oil (88.5% of the expected saturated conjunct polymers). The total conjunct polymers removed by hydrogenation over Ni—Al at 100° C. and 500 psi $H_2$ pressure was 94%.

Example 16

Example 15 above was repeated with 50 gm of spent ionic liquid containing 24.3 wt % (12.15 gm) conjunct polymers in 70 cc hexane in the presence of 3 gm of Ni—Al alloy at 100° C. and starting hydrogen pressure of 500 psi. The reaction ran for 1.5 hrs. A total of 11.5 gm (94.6%) conjunct polymers were removed from the spent catalyst based on obtained saturated polymers and recovered CPs from the hydrolysis of 10 gm portion of the treated ionic liquid catalyst. The remainder of the treated ionic liquid catalyst was saved and tested for activity as described in example 12.

Example 17

Hydrogenation of Conjunct Polymers in Spent Chloroaluminate Ionic Liquid Catalyst over Nickel Metal As in Example 15 above, 25 gm of spent chloroaluminate ionic liquid catalyst containing 15.5 wt % (3.87 gm) conjunct polymers in 60 ml anhydrous hexane (in 300 cc autoclave) was hydrogenated at 100° C. and 500 psi hydrogen pressure over Nickel metal (3 gm) for 1.5 hours. Once the heating started, the pressure steadily started rising until it reached 946 psi at 100° C. The pressure dropped slightly to 910 psi at the end of the run. The reaction was stopped and the organic phase containing the hydrogenated polymers was decanted off. The ionic liquid-Ni residue was rinsed with 2×50 ml anhydrous hexane. All the organic layers were combined and dried over MgSO4. Filtration and concentration to remove hexane gave 1.58 gm (41%) of the hydrogenated polymers as colorless oil. The ionic liquid catalyst was separated from Nickel metal by filtration. The ionic liquid catalyst was entirely hydrolyzed giving 1.62 gm conjunct polymers (the total amount of CPs remaining in the catalyst). This indicates that hydrogenation over Nickel metal led to the overall removal of 2.2 gm (58%) of the conjunct polymers from the spent catalyst.

Example 18

Determination of the Activity of the Regenerated ButylPyridinium Chloroaluminate Ionic Liquid Catalyst by Hydrogenation over Ni—Al Alloy The regenerated butylpyridinium chloroaluminate ionic liquid catalyst described in Examples 15 and 16 was tested for activity by using it as the catalyst in the alkylation of isopentane with ethylene and comparing it with freshly-made catalyst. The alkylation of isopentane with ethylene was done according to the following procedure A 300 cc autoclave was charged with 20 gm of ionic liquid catalyst, 100 gm anhydrous isopentane, 10 gm ethylene and 0.3 gm anhydrous HCl. The reaction was then stirred ~1200 rpm and heated to 50° C. at autogenic pressures. The starting pressure was usually 280-320 psi. The reaction was usually complete when the pressure dropped down to single digits. In the case of slow going reaction, the reaction was allowed to go on for 1 hr. At the end of the reaction, the reactor was vented out and a gas sample was checked by GC for ethylene concentration. The liquid reaction mixture was allowed to settle into 2 phases. The organic phase was decanted and analyzed for product distribution by GC analysis. The following Table 3 draws a comparison among the freshly made, the spent and the regenerated catalysts.

TABLE 3

|  | Fresh Ionic Liquid Catalyst | Spent Ionic Liquid Catalyst | Ni—Al Regen. Ionic Liquid Cat. |
|---|---|---|---|
| Reaction Time | 6-9 min. | 60 min. | 4-7 min. |
| Starting Pressure | 300 psi | 286 psi | 350 psi |
| Ending pressure | 11 | 302 psi | 7 |
| iC5 wt % | 72 | 98 | 61 |
| C7s wt %: |  |  |  |
| 2,3-DM-Pentane | 8.23 | 0.9 | 8.5 |
| 2,4-DM-Pentane | 10 | 0.6 | 11.3 |
| Other C7s | 0.77 | 0.1 | 1.2 |
| 2,3DM/2,4DM | 0.82 | 1.5 | 0.75 |

Example 19

Removal of Conjunct Polymer from Deactivated IL A by Reaction with Isobutane

Deactivated IL A (14.50 gm) containing ~18 wt % conjunct polymer was charged to a nitrogen-filled 100 mL autoclave. Ten milliliters of HCl gas measured at ambient temperature and pressure were added to the autoclave. The autoclave was then filled with liquid isobutane (81.6 gm) at ambient temperature.

The autoclave was heated to 100 C with stirring for 5 hours, then cooled to ambient temperature. In a drybox, the ionic liquid was removed and extracted with hexane to remove saturated conjunct polymer.

To measure the removal of conjunct polymer, 7.56 grams of the recovered ionic liquid were hydrolyzed. The resulting aqueous mixture was extracted with hexane. After evaporation of hexane, 0.60 grams remained, indicating that after reaction with isobutane and HCl, the ionic liquid contained 7.9 wt % conjunct polymer. This means that the treatment with isobutane and HCl removed ~57% of the conjunct polymer originally present in the used ionic liquid catalyst.

There are numerous variations on the present invention which are possible in light of the teachings and supporting examples described herein. It is therefore understood that within the scope of the following claims, the invention may be practiced otherwise than as specifically described or exemplified herein.

What is claimed is:

1. A process for regenerating a used acidic ionic liquid catalyst which has been deactivated by conjunct polymers in a reactor,
comprising removing the conjunct polymers by an alkylation with an isoparaffin feedstock in the presence of a Broensted acid in a separate regeneration reactor so as to increase the activity of the catalyst; and
wherein the isoparaffin feedstock is used to reactivate the used acidic ionic liquid catalyst.

2. The process according to claim 1, wherein the used acidic ionic liquid catalyst has been used to catalyze a Friedel-Craft reaction.

3. The process according to claim 2, wherein the Friedel-Craft reaction is alkylation.

4. The process of claim 1, wherein the used acidic ionic liquid catalyst comprises an imidazolium, a pyridinium, a phosphonium or a tetralkylammonium derivative or their mixtures, or wherein the used acidic ionic liquid catalyst is a chloroaluminate ionic liquid; and wherein the used acidic ionic liquid catalyst which has been deactivated by conjunct polymers is introduced continuously into the regeneration reactor.

5. A process for regenerating a used acidic ionic liquid catalyst which has been deactivated by conjunct polymers in a reactor,
comprising removing the conjunct polymers by an alkylation with an isoparaffin feedstock in the presence of a Broensted acid, wherein the isoparaffin feedstock is used to reactivate the used acidic ionic liquid catalyst;
wherein the removing is done in a separate regeneration reactor so as to increase the activity of the catalyst;
wherein the used acidic ionic liquid catalyst comprises an imidazolium, a pyridinium, a phosphonium or a tetralkylammonium derivative or their mixtures, or wherein the used acidic ionic liquid catalyst is a chloroaluminate ionic liquid; and
wherein the used acidic ionic liquid catalyst which has been
deactivated by conjunct polymers has a level of conjunct polymers that is at least 15.5 wt %.

6. The process according to claim 5, wherein the used acidic ionic liquid catalyst has been used to catalyze a Friedel-Craft reaction.

* * * * *